US00PP14552P29

(12) United States Plant Patent
Pierce

(10) Patent No.: US PP14,552 P2
(45) Date of Patent: Feb. 17, 2004

(54) CALIBRACHOA PLANT NAMED 'CAL DARBLU'

(50) Latin Name: *Calibrachoa spp.*
Varietal Denomination: Cal Darblu

(75) Inventor: Robert Osteen Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/389,094
(22) Filed: Mar. 13, 2003
(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A Para
(74) *Attorney, Agent, or Firm*—Jondle & Associates, PC

(57) ABSTRACT

'Cal Darblu' is a new variety of Calibrachoa plant. This new variety has dark blue colored flowers.

1 Drawing Sheet

Genus and species: Calibrachoa spp.
Variety denomination: 'Cal Darblu'.

BACKGROUND OF THE INVENTION

'Cal Darblu' originated from a hybridization made in the year 2000 in Gilroy, Calif. The female parent was a Calibrachoa breeding line with lavender rose colored flowers known as 162-2 a proprietary line unnamed and unpatented. The male parent was Calibrachoa variety 114-1, a blue proprietary line unnamed and unpatented.

'Cal Darblu' is a product of a planned breeding program intended to create new calibrachoa plants with dark blue colored flowers, compact habit, good basal branching and moderately vigorous growth.

The new cultivar was created in 2000 in Gilroy, Calif. and has been asexually reproduced repeatedly by vegetative cuttings and tissue culture in Gilroy, Calif., Andijk, The Netherlands, and Guatemala over a 2 and half-year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF THE GENUS CALIBRACHOA LLAVE & LEX

The genus Petunia was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for Petunia in 1913.

During the 1980's and 1990, H. J. Wijsman published a series of articles regarding the ancestry of P. hybrida, the Garden Petunia, and the inter-relationship of several species classified as Petunia. These studies discovered that P. hybrida and its ancestrial species, *P. nyctaginiflora* (=*P. axillaris*) and *P. violacea* (=*P. integrifolia*), possessed 14 pairs of chromosomes while several other species, including *P. parviflora,* possessed 18 pairs of chromosomes. Since *P. parviflora* was the lectotype species for the Petunia genus, Wijsman and J. H. de Jong proposed transferring the 14 chromosome species to the genus Stimoryne. Horticulturists opposed reclassifying the Garden Petunia and in 1986, Wijsman proposed the alternative of making *P. nyctaginiflora* the lectotype species for Petunia and transferring the 18 chromosome species to another genus. The I. N. G. Committee adopted this proposal. By 1990 Wijsman had transferred several species, including *P. parviflora* (=*C. parviflora*) to Calibrachoa, originally established by Llave and Lexarza in 1825. *Calibrachoa parviflora* (=*C. mexicana* Llave & Lexarza) is now the type species for the genus Calibrachoa.

Classification of the current Petunia and Calibrachoa species is still in progress. New species are also being identified. Consequently a proper description has not been written for the Calibrachoa genus. Calibrachoa can, however, be distinguished from Petunia based on the higher chromosome number, chromosome morphology, plant branching habit and type of flower bud aestivation. Whereas Petunia species bear a flower peduncle and one new stem from a node, Calibrachoa bear a flower peduncle and three stems. Petunia species have a cochlear corolla bud, a single outermost petal covers the other four, radially folded and terminally contorted petals. Calibrachoa flower buds are flat with all five petals linearly folded and the two lower petals forming a cover around the three other petals and fused together.

DETAILED DESCRIPTION OF THE NEW PLANT

The following traits and characteristics describe the new variety. The plant history was taken on 7 month old plants that were cut back numerous times prior to data readings being taken.

Classification:
- *Family.*—Solanaceae.
- *Species.*—Calibrachoa spp.

Growth:
- *Form.*—Semi upright and decumbent.
- *Habit.*—Good vigorous habit, well branched, full plant.
- *Height.*—5–10 cm.
- *Width.*—50–60 cm.
- *Time to produce a finished flowering plant.*—8–10 weeks.

*Outdoors plant performance.*—Full sun, free flowering through the summer, some heat tolerance, used as a hanging plant, in mixed container plantings, flower boxes, mass planting in a bed.
*Time to initiate and develop roots.*—18–23 days.
*Rood description.*—White, fibrous.

Stems:
*Stem color.*—RHS 144B (yellow-green).
*Stem length.*—60–70 cm.
*Stem diameter.*—0.15–0.25 cm.
*Stem internodes length.*—0.5–1.0 cm.
*Stem texture.*—Very short glandular hairs.
*Stem anthocyanin.*—None.
*Pedicel color.*—RHS 144A (yellow-green).
*Pedicel length.*—2.1–2.4 cm.
*Pedicel diameter.*—0.1 cm.
*Pedicel texture.*—Very short glandular hairs.

Leaves:
*Arrangement.*—Alternate, upper leaves sub-opposite.
*Leaf color.*—Upper side, RHS 137B (green). Underside, RHS 138A (green).
*Leaf length.*—2.4–3.9 cm.
*Leaf width.*—1.3–2.1 cm.
*Leaf blade shape.*—Elliptic.
*Leaf margin.*—Entire.
*Leaf apex aspect.*—Acute/Obtuse.
*Leaf bas aspect.*—Acuminate.
*Leaf texture.*—Very short glandular hairs.
*Venation.*—Pinnate.
*Venation color.*—RHS 144B (yellow-green).
*Petiole color.*—RHS 144B (yellow-green).
*Petiole length.*—0.1–0.3 cm.
*Petiole width.*—0.1–0.15 cm.
*Petiole texture.*—7 Very short glandular hairs.

Bud:
*Color at tight bud.*—RHS N186C (greyed-purple).
*Bud shape.*—Oblong.
*Bud diameter.*—0.3–0.4 cm.
*Bud length.*—1.7–2.0 cm.

Flowers:
*Blooming habit.*—Continuous throughout the growing season. Good floriferousness.
*Inflorescence type.*—Flowers solitary in upper leaf axis.
*Floret type.*—Funnel form, 5 lobed petals, fused at base.
*Young flower color.*—Close between RHS 83A/B (violet); RHS N92A (violet-blue) mid-veins.
*Floret diameter.*—2.7–2.9 cm.
*Mature flower color.*—Front side, closest to RHS 83B (violet) base color; RHS N92A (violet-blue) mid-veins; RHS 79C (purple) secondary veins.
*Mature flower color.*—Underside, RHS 83D (violet); RHS 83A (violet) mid-veins.
*Corolla tube color inside.*—RHS 3A (yellow); RHS N77A (purple) and RHS N77C (purple) veining.
*Corolla tube length.*—1.5–1.7 cm.
*Corolla outside texture.*—Very short glandular hairs.
*Flower (limb) diameter.*—2.9–3.2 cm.
*Petal apex shape.*—Retuse.
*Petal base shape.*—Fused.
*Petal margin.*—Entire.
*Waviness of petals.*—Weak.
*Petal lobation.*—Moderate.
*Petal texture.*—Papillose.
*Sepals.*—5.
*Sepal color.*—RHS 138B (green).
*Sepal length.*—0.5–0.6 cm.
*Sepal width.*—0.3–0.4 cm.
*Sepal shape.*—Oblong.
*Sepal apex.*—Acute.
*Sepal texture.*—Very short glandular hairs.
*Lastingness of individual blooms.*—4–8 days.
*Fragrance.*—None.

Reproductive organs:
*Stamens.*—5, 2 taller, 2 shorter, 1 very short.
*Filament color.*—RHS 145D (yellow-green).
*Pollen color.*—RHS 8B (yellow).
*Pistil.*—One.
*Stigma color.*—RHS 143C (green).
*Style color.*—RHS 145C (yellow-green).
*Fruit seed set.*—Not observed.

COMPARISON WITH MOST SIMILAR VARIETY

'Cal Darblu' differs from the female parent 162-2 in the following ways: Cal Darblu has a dark blue flower and 162-2 has a lavender rose flower. 'Cal Darblu' has smaller leaves and is more prostrate in habit than 162-2.

'Cal Darblu' differs from the male parent 117-1 in the following ways: 'Cal Darblu' has smaller flowers than 114-1. 'Cal Darblu' flowers earlier and is more center flowering than 117-1.

What is claimed is:

1. A new and distinct Calibrachoa plant as shown and described herein.

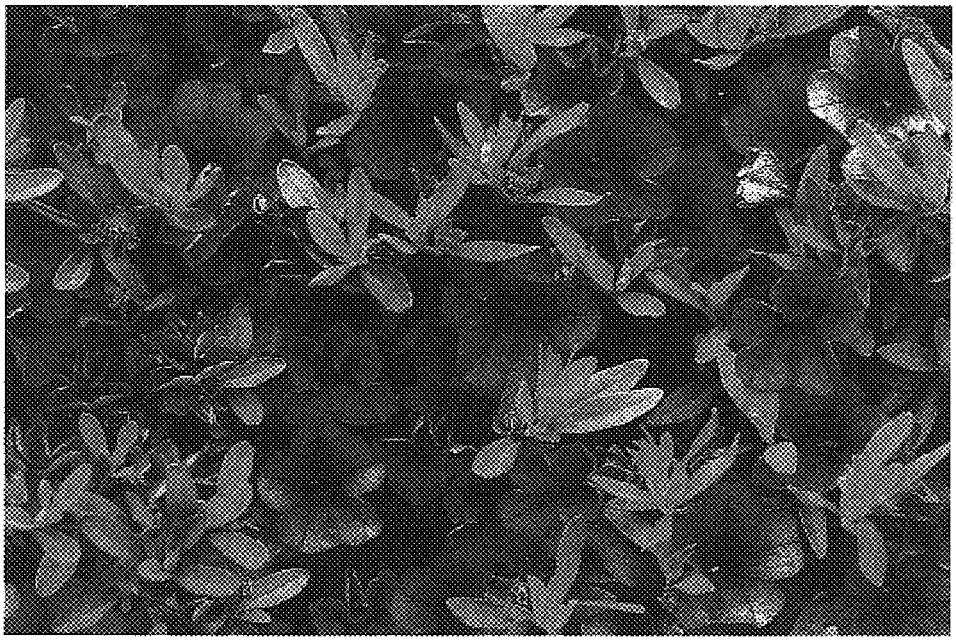

* * * * *